Figure 1:
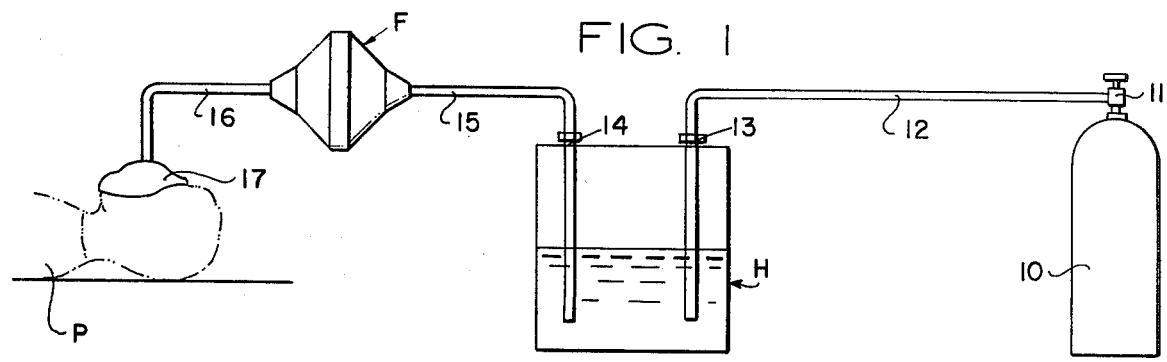

United States Patent [19]

Chapel

[11] 4,128,407
[45] Dec. 5, 1978

[54] STERILE OXYGEN SYSTEM AND REPLACEABLE FILTER THEREFORE

[75] Inventor: James F. Chapel, 1019 Ridgecrest Cir., Denton, Tex. 76201

[73] Assignees: James Frederick Chapel, Denton; Homer C. Harper, III, Dallas, both of Tex.; Michael F. Coyne, San Francisco, Calif.

[21] Appl. No.: 627,931

[22] Filed: Nov. 3, 1975

[51] Int. Cl.$^2$ .............................................. B01D 53/00
[52] U.S. Cl. ................................. 55/259; 55/DIG. 33; 210/501
[58] Field of Search ................... 55/256, 259, 97, 487, 55/DIG. 33; 128/186, 187, 202, 195; 261/DIG. 65, 121 R; 210/501

[56] References Cited

U.S. PATENT DOCUMENTS

| | | | |
|---|---|---|---|
| 2,166,574 | 8/1939 | Adolphsen | 261/122 X |
| 3,140,590 | 7/1964 | Gleockler | 55/DIG. 33 |
| 3,556,097 | 1/1971 | Wallace | 128/188 |
| 3,667,463 | 6/1972 | Barnes | 261/DIG. 65 X |
| 3,672,129 | 6/1972 | Strople et al. | 55/270 |
| 3,912,795 | 10/1975 | Jackson | 128/186 |

Primary Examiner—Charles N. Hart
Assistant Examiner—E. Rollins Cross
Attorney, Agent, or Firm—Hubbard, Thurman, Turner, Tucker & Glaser

[57] ABSTRACT

A system and filter apparatus therefore are described for providing substantially bacteria-free, humidified oxygen to a breathing mask or breathing tube. The filter apparatus is hydrophobic and is inserted either at or adjacent the outlet of a humidifier, in the flow line between the outlet of the humidifier and the breathing mask, or at or adjacent the breathing mask, and can be easily replaced when contaminated after a period of use.

21 Claims, 7 Drawing Figures

STERILE OXYGEN SYSTEM AND REPLACEABLE FILTER THEREFORE

This invention relates to the sterilization of humidified oxygen in a life support system and in one if its aspects to a system and replaceable filter apparatus therefore for providing substantially bacteria-free, humidified oxygen to a breathing mask or breathing tube.

Within the hospital patient care system, the use of oxygen for therapeutic purposes is well known. In most instances the oxygen must be humidified with water prior to patient inhalation in order to prevent drying of the mucous membranes of the air passages of the patient.

Currently, the humidification of oxygen is most commonly accomplished by sparging the oxygen gas through a column of water. A result of this sparge is cavitation and turbulence within the humidifier reservoir yielding particulate as well as molecular water. As is documented, the particulate aerosol thus generated is capable of entraining waterborne bacteria. For example, in *Hospital Infection Causes and Prevention* by R. E. O. Williams, M.D. et al., Second Edition, 1966, it is noted at Page 253 that a ten-fold increase in the frequency of necrotizing pneumonia occurred during a period of eleven years just prior to 1965 due to the increase in the use of inhalation therapy during that period.

At present, it is common for hospitals to use either (i) pre-filled, sterile, disposable humidifiers, (ii) non-sterile disposable humidifiers, or (iii) permanent humidifiers which must be frequently sterilized, at least for each separate patient use. The pre-filled, sterile humidifier generally includes a plastic bottle with a built-in sparge which is either terminally sterilized or aseptically filled, and is a relatively expensive "single patient use" item, and even with its use, contamination can result if the oxygen supply or regulating equipment contains bacteria since no filtering is provided.

Both the permanent and disposable non-sterile humidifiers (and associated equipment) must be sterilized by hospital personnel before use, must be filled with specially prepared or purchased sterile water, and also do not prevent contamination where the oxygen or regulating equipment contains bacteria. Recommended hospital procedure for these devices is daily cleaning with acetic acid and distilled water, and, despite these precautions, the apparatus can become recontaminated fairly quickly. See *Hospital Infection Causes and Prevention* referenced above at page 254.

The authors of that book also suggest at page 254 that the additional precaution of a bacterial filter in the airstream immediately before reaching the patient would be useful, but point out that at the time of that writing all available filters were easily blocked by condensation and are therefore unsuitable to meet their suggestions. In so far as is known to applicant, this fact remains true today.

By way of example, U.S. Pat. No. 3,672,129 illustrates a portable sterilizer which is to be placed between a standard oxygen container and a patient's oxygen mask to supply the patient with a controlled rate of flow of sterilized oxygen, or if a humidifier were used, between the oxygen source and the humidifier. The unit described, and the filter utilized, which requires a pressure regulated flow of gas, are not adapted for, and would not be suitable for, sterilization of humidified oxygen in which the relative humidity may exceed 90%.

It is thus the primary object of this invention to provide a system for supplying humidified, substantially bacteria free oxygen for life support even though the oxygen, oxygen regulating equipment, or the humidifying apparatus may not be sterile.

Another object of this invention is to provide such a system which does not require frequent, periodic sterilization of the various components of the system, or the use of relatively expensive, disposable "single patient use" items.

Another object of this invention is to provide such a system which includes a bacteria filter adapted to be inserted in the system to sterilize the particulate aerosol containing waterborne bacteria prior to inhalation by a patient or other subject.

Another object of this invention is to provide such a filter which is relatively inexpensive, disposable when contaminated sufficiently to no longer be useful, and which can be adapted to be inserted in line in portable or permanent life support system at any convenient location between the source of the particulate aerosol and the patient or other subject.

Another object of this invention is to provide such a filter which can be used for a relatively long period of time before disposal and replacement is required, and which does not become clogged by the moisture of the aerosol.

In the design of a bacteria filter such as described, and such as provided by this invention, it is preferred that the filter meet or surpass each of the following requirements; i.e.

1. The filter should be capable of producing bacteria-free oxygen at an efficiency of at least about 99.0% for a minimum of about 24 hours at any reasonable flow rate.
2. The filter should not reduce the relative humidity of the respective humidifier by more than about 1.0%.
3. The pressure drop for the filter should not exceed about 1.0 psi over the use range for the 24 hour period.
4. There should be no flow direction requirement for the filter.
5. The filter should be capable of use with accepted commercial humidifiers, and
6. The filter should be capable of being sterilized and be sold as a sterile unit.

It is thus another object of this invention to provide a filter which can meet or surpass each of these requirements and be a commercially accepted device.

These and other objects of this invention, which will become apparent upon consideration of the appended drawings and claims and the detailed description of the drawings to follow, are accomplished by this invention by providing a humidified oxygen life support system generally including a source of oxygen, a humidifier, a breathing mask of breathing tube and connecting tubing, and a bacteria filter therefore. The filter is hydrophobic and adapted to be removably inserted in the life support system at any place between the point where a bacteria containing aerosol is generated, generally adjacent the outlet of the humidifier, and the point of inhalation by a subject, generally adjacent the breathing mask or breathing tube. The filter preferably includes a filter pad having a plurality of alternate layers of coarse and fine weave hydrophobic material, such as glass, mounted in a filter housing with the multiple layers of the fine weave material adapted to trap bacteria, and the multiple layers of the coarse weave material functioning as support for the filter pad. It is preferred that the filter pad include sufficient layers of the fine weave material so that trapped bacteria on the first or subsequent layers of fine weave material is retarded from "growing through" the filter pad by subsequent layers of fine weave material and thus spilling over into the filtered oxygen stream.

Figures 2, 3, 4, 5:
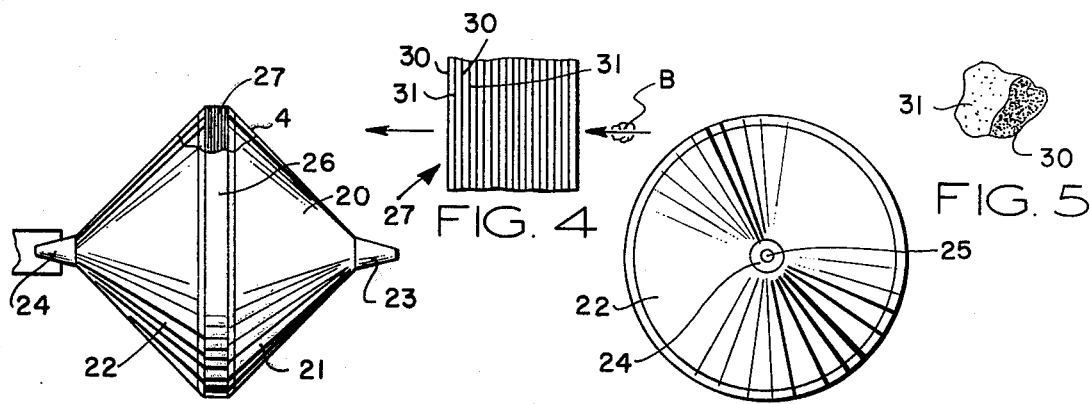
Figure 6:
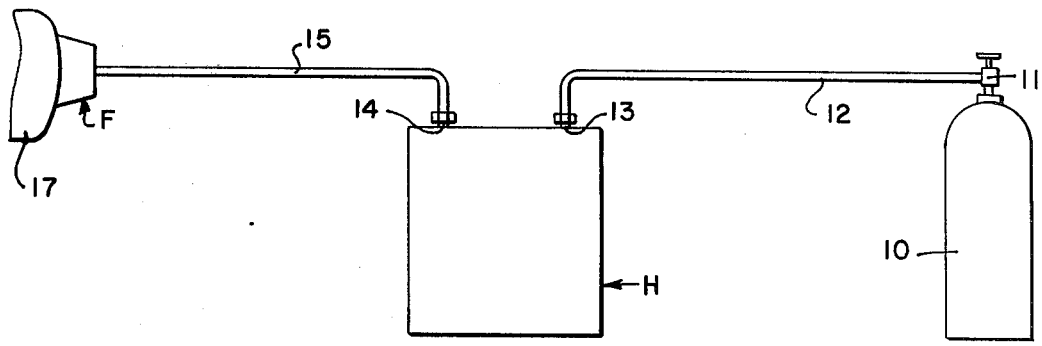
Figure 7:
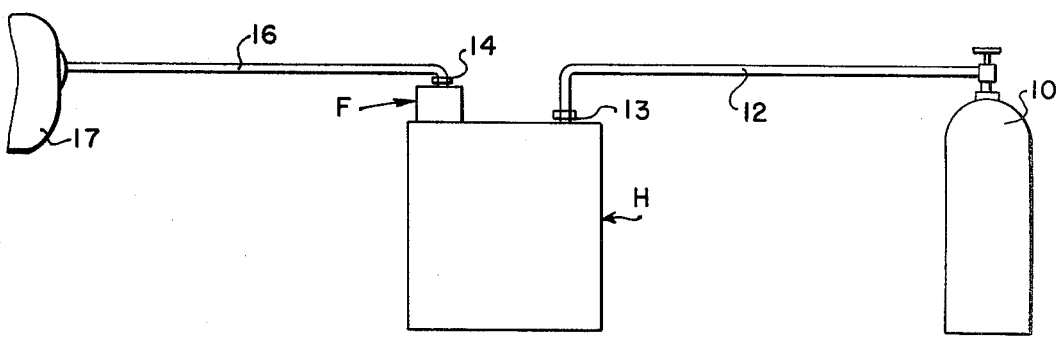

In the drawings wherein like reference numerals are used throughout to designate like parts, and wherein preferred embodiments of this invention are shown;

FIG. 1 is a side view in elevation of the overall system of this invention employing a bacteria filter, FIG. 2 is a side view in elevation of the bacteria filter of FIG. 1, FIG. 3 is an end view of the filter of FIG. 2, FIG. 4 is an enlarged view of the layered filter pad taken at 4 in FIG. 2, FIG. 5 is a partial front view in partial cut away of the filter pad of FIG. 4, FIG. 6 is a side view in elevation of another embodiment of the system of this invention, and FIG. 7 is a side view in elevation of still another embodiment of the system of this invention.

Referring now to the drawings, in FIG. 1, an oxygen life-supporting system is illustrated as including a source of oxygen 10 having a valved outlet 11 connected through a conduit 12 to the inlet 13 of a humidifier H, which may be one of many commercial-type humidifiers available on the market, such as illustrated in U.S. Pat. Nos. 2,709,577; 2,166,574; and 2,267,009. Humidifier H includes an outlet 14, through which humidified oxygen having a relative humidity generally in excess of 90% is conducted by conduit 15, to one side of a bacteria filter F to be described with reference to FIGS. 2 through 5. Humidified oxygen in conduit 15 may include particulate aerosol containing bacteria B which is filtered in filter F, and the substantially bacteria-free humidified oxygen passes out of filter F through conduit 16 to a breathing mask 17, where it is inhaled by a patient P, as illustrated in FIG. 1. The system described is conventional, except for the inclusion of filter F between conduits 15 and 16, for the purpose of removing the bacteria containing areosol to provide a substantially bacteria-free humidified oxygen to the patient.

The system described is representative of either a portable life-support system which may be used in an emergency vehicle or in other emergency situations, or a permanent life-support system in a hospital, or other place where humidified oxygen is required for sustaining life.

The details of a preferred form of filter F are illustrated in FIGS. 2 through 5. It is preferred that filter F be a presterilized, disposable unit, which can be readily inserted in the system of FIG. 1, such as between conduits 15 or 16, or at any place in the system between the point at which the bacteria containing aerosol is generated and inhalation occurs. Filter F may be inexpensively made with a molded plastic housing 20, comprising identical conical shaped portions 21 and 22, and nipples 23 and 24 respectively having an opening 25 therethrough, for the receipt or discharge of humidified oxygen and for the connection to tubing.

An important feature of the present invention is that filter F is preferably designed to be bi-directional so that either of nipples 23 or 24 can function as the inlet or the outlet of the filter. Filter F also includes a central, circular band 26 which also may be made of plastic, which supports a filter pad 27, between nipples 23 and 24, so that as oxygen passes from one of the nipples to the other it must pass through filter pad 27. Filter F can be constructed so that filter pad 27 is an integral part of band 26, and by removing housing portion 21 and 22, a new band and new filter pad may be inserted. However, if this is done, portions 21 and 22 of housing 20 must be sterilized again and it is preferred that the entire filter element F be disposed of when pad 27 becomes sufficiently contaminated with bacteria. However, tests have indicated that under normal usage, filter F may be used in excess of 24 hours before it is necessary to discard it and replace it with a new filter.

If filter F is made disposable, then the various components can be glued or coupled together by epoxy to form a rigid unit. Also, the filter pad should be sealed about its edges and between these edges and the inner wall of housing 20 so that all oxygen passing through filter F must pass through pad 27.

FIGS. 4 and 5 illustrate the details of a preferred form of pad 27, for use in Filter F. Filter pad 27 must be capable of removing particulate material, such as bacteria from a wet oxygen stream, and preferably must consist of a plurality of layers of support material and filtering material, with preferably four or more layers of filling material provided. In the embodiment illustrated in FIG. 4, eighteen layers of support and filtering material are provided and the ordering of the layers is important. As illustrated in FIGS. 4 and 5, it is preferred that every other layer 30 be a support layer of relatively coarse woven material, such as rayon, nylon or other fully hydrophobic material, and the in-between layers 31 be of a relatively fine weave glass material such as disks cut from sheets of randomly woven glass material having a bacteria retention capability of in excess of about 95%. This sequence is repeated for the total eighteen layers to provide a filter pad having a bacteria retention capability in excess of the capability of each individual layer and generally in the order of 99.0% to 100%. In the embodiment described having eighteen layers, the majority of the filtration is accomplished in the first nine layers of filter pad 27 exposed to the flow of oxygen, with the remaining nine layers acting to retard "grow-through" and subsequent spill over into the filtered oxygen stream. More or fewer layers can be used depending on the requirements of a specific system as long as the six requirements set out earlier for a bacteria filter are substantially met.

Also of importance in this filter is the use of hydrophobic filter material in order to minimize wetting and concomitant increase in backpressure. Also, all commercially available humidification devices are equipped with pressure relief valves which actuate at approximately two psi backpressure, and the described bacteria filter pad was designed to have a maximum backpressure of about 0.8 psi within the oxygen flow ranges commonly used in patient support and therapy.

In actual use of the system of this invention, a number of tests were made to illustrate the removal of bacteria from humidity-laden oxygen gas by stream filtration with filter constructed in accordance with this invention.

To any one of several different commercial humidifiers was added 250 ml of either tap water or tap water containing varying concentrations of microorganisms (concentration range from $10^2$–$10^4$ cells/ml). Various bacteria filters with pads constructed in accordance with that illustrated in FIGS. 2–5 were interposed between the humidifier and a 3% tryptic soy broth (TSB)

receiver. The humidifier was then sparged at 1.0 liters per minute and various times and the effluent stream collected by secondary sparging into the TSB receiver. The TSB was then incubated at room temperature or at 37° C. for up to five days. Both positive and negative controls were run simultaneously.

Secondly, routine dilution plate counts or direct counts on "Millipore" membrane were made on the tap water samples in order to establish the bacterial burden which could be expected in the humidifier reservoirs.

The bacterial burden as determined for the course of these experiments, was at all times greater than $10^2$ cell/ml with a mean value of $2.7 \times 10^2$, a low range of $2.2 \times 10^2$ and a high range of $3.7 \times 10^4$.

The ability of the filters to remove bacteria from gas streams humidified with tap water is summarized in Table A as follows:

TABLE A

The effect of the humidifier filter on the transfer of bacteria from sparged tap water.

| Flow Rate, lpm | Sparge Time, hrs. | Growth |
|---|---|---|
| 1 | 36 | + |
| 1 | 30 | + |
| 1 | 24 | − |
| 1 | 24 | − |
| 1 | 24 | − |
| 1 | 18 | − |
| 1 | 18 | − |
| 1 | 30 | + |
| 1 | 26 | − |
| 1 | 24 | − |
| 1 | 24 | − |
| 1 | 24 | − |
| 1 | 24 | − |
| 1 | 24 | − |
| 1 | 36 | + |
| 1 | 36 | + |
| 1 | 24 | − |
| 1 | 24 | − |
| 1 | 24 | − |

+ = Growth
− = No Growth

A similar experiment, but one in which the sparge times were interrupted by cycles of incubation is given in Table B.

TABLE B

Bacterial retention of humidifier filter as a function of sparge time at 1 lpm flow.

| Time Hours | | Growth (G)/No Growth (NG) | |
|---|---|---|---|
| Flask #1 | Flask #2 | Flask #1 | Flask #2 |
| 18 | 18 | N.G. | N.G. |
| | 24 | — | N.G. |
| 7 | 7 | N.G. | G |

Total time before growth occurred:

| Flask #1 | Flask #2 |
|---|---|
| N.G. at 25 hours | N.G. at 42 hours |

As may be seen from Tables A and B, the humidifier filter of this invention is substantially 100% efficient for the removal of bacteria at a flow rate of 1 lpm for 24 hours, and meets the efficiency requirements set out earlier in this specification as required for a substantially bacteria free oxygen life support system.

In view of the fact that all commercial humidifiers are designed with a safety pop off valve, it is important that the humidifier filter of this invention be designed such that its backpressure is low enough that it does not trigger the pop off valve. In addition, since the flow of oxygen delivered to any given patient varies, the backpressure of the filter must be considered for various flow rates. Tests were also conducted comparing the backpressure versus flow rate for the filter for two different relative humidities. The data from that test show that the backpressure is a linear function of the flow rate. Further, on the basis of this data, it was established that at the flow rates involved in the conventional oxygen life support system the backpressure is substantially less than the upper acceptable limit of 1.0 psi, set as a maximum permissible backpressure for the filter of this invention, and, in fact, was below this value for flow rates of from 1 lpm to about 14.0 lpm during the test conducted.

Also, tests were conducted to determine if the humidifier filter had any detrimental effect on the relative humidity equilibrium of the oxygen system, recording the time in minutes or seconds required for the relative humidity equilibrium to be established at two different flow rates when a filter is in line with the humidifier. Comparison of this data indicates that the time required for the humidifier to supply a high relative humidity when a filter is in place is not sufficiently greater than for a humidifier by itself. In all cases, the rise time to relative humidity equilibrium compared both with and without a filter in place did not exceed about five minutes, and this five minute time period can be easily tolerated by a human patient receiving oxygen from the system.

Also, once equilibrium for a particular flow rate has been established, comparison of the absolute difference between the relative humidity output of the humidifier both with and without a filter in place demonstrated that the filter does not effect the final relative humidity value of the system, and, that the equilibrium humidity value is generally a function of the humidifier itself and not the bacteria filter.

In order to further evaluate the effects of relative humidity on backpressure in the tests conducted, the relative humidity was plotted as the independent variable against backpressure for various fixed flow rates. This data indicated that with a filter pad 27 such as described with respect to FIGS. 2–5, relative humidity does not effect the backpressure to any significant degree within reasonable limits of flow.

Thus, it should be readily apparent that a suitable bacteria filter meeting all of the requirements for sterilizing humidified oxygen in a life support system is provided by the present invention. The bacteria filter can be readily placed in existing oxygen systems between a humidifier and the breathing mask, or at the outlet of the humidifier or the inlet of a breathing mask, or in a complete oxygen system provided with the filter incorporated as an integral part thereof.

From the foregoing, it will be seen that this invention is one well adapted to attain all of the ends and objects hereinabove set forth, together with other advantages which are obvious and which are inherent to the apparatus.

It will be understood that certain features and subcombinations are of utility and may be employed without reference to other features and subcombinations. This is contemplated by and is within the scope of the claims.

As many possible embodiments may be made of the invention without departing from the scope thereof, it is to be understood that all matter herein set forth or shown in the accompanying drawings is to be interpreted as illustrative and not in a limiting sense.

What is claimed is:

1. A system for providing substantially bacteria free humidified oxygen to a respiratory system, comprising in combination:
   a source of pressurized oxygen;
   a humidifier including a gas inlet connected in fluid communication to said source, a reservoir of liquid, a gas-liquid outlet and means for humidifying said oxygen while passing oxygen from said inlet through said liquid and out of a gas-liquid outlet;
   means connected in fluid communication to said outlet and adapted to provide oxygen to said respiratory system; and
   sterile, disposable filter means connected between said last mentioned means and said means for humidifying said oxygen, said filter means being capable of removing a substantial amount of bacteria from humidified oxygen while providing a relatively small increase in back pressure to the flow of humidified oxygen due to wetting, whereby humidified, substantially bacteria free oxygen can be supplied for life support even though the oxygen, oxygen regulating equipment, or the humidifying apparatus is not sterile; and
   said filter means includes housing having an inlet and an outlet to which tubing can be detachably connected and a filter pad, located in said housing between said inlet and said outlet, containing multiple layers each of a hydrophobic support material and a hydrophobic bacteria filtering material.

2. The system of claim 1 wherein said support material is made from a group of material consisting essentially of nylon or rayon.

3. The system of claim 1 wherein said filtering material is made of a relatively close, randomly woven, sheet glass material.

4. The system of claim 3 wherein said support material is made from a group of material consisting essentially of nylon or rayon.

5. The system of claim 1 wherein said layers of filtering material are sufficient in number to retain in excess of 99.0% of the bacteria in a humidified oxygen stream passing through said filter in a first group of said layers, and retard grow through of said retained bacteria in a second group of said layers of filtering material.

6. The system of claim 5 wherein at least four layers of said filtering material are provided.

7. The system of claim 6 wherein said support material is made from a group of material consisting essentially of nylon or rayon.

8. The system of claim 6 wherein said filtering material is made of a relatively close, randomly woven, sheet glass material.

9. The system of claim 8 wherein said support material is made from a group of material consisting essentially of nylon or rayon.

10. A disposable bacteria, hydrophobic filter for connection in a humidified oxygen support system comprising, in combination:
    a housing including an inlet and an outlet; and
    a hydrophobic filter medium mounted in said housing between said inlet and said outlet, the connection between said housing and said filter medium being sufficiently sealed to prevent substantial leakage of gas passing through said housing and cause substantially all of said gas to pass through said filter medium, said filter medium including a plurality of layers of hydrophobic filtering material and a plurality of layers of hydrophobic supporting pads, said layers of filtering material being sufficient in number to retain in excess of 99.0% of the bacteria in a humidified oxygen stream passing through the filter in a first group of said layers, and retard grow through of said retained bacteria in a second group of said layers of said filtering materials, whereby the filter can be readily placed in and removed from the life support system so that humidified, substantially bacteria free oxygen can be supplied for life support even though the oxygen, oxygen regulating equipment, or the humidifying apparatus is not sterile.

11. The filter of claim 10 wherein at least four layers of said filtering material are provided.

12. The filter of claim 10 wherein said support material is made from a group of material consisting essentially of nylon or rayon.

13. The filter of claim 10 wherein said filtering material is made of a relatively close, randomly woven, sheet glass material.

14. The filter of claim 13 wherein said support material is made from a group of materials consisting essentially of nylon or rayon.

15. A system for providing substantially bacteria free humidified oxygen to a respiratory system, comprising in combination:
    a source of pressurized oxygen;
    a humidifier including a gas inlet connected in fluid communication to said source, a reservoir of liquid, a gas-liquid outlet and means for humidifying said oxygen while passing oxygen from said inlet through said liquid and out of a gas-liquid outlet;
    means connected in fluid communication to said outlet and adapted to provide oxygen to said respiratory system; and
    sterile, disposable filter connected between said last mentioned means and said means for humidifying said oxygen, said filter being capable of removing a substantial amount of bacteria from humidified oxygen while providing a relatively small increase in back pressure to the flow of humidified oxygen due to wetting, said filter including a housing inluding an inlet and an outlet, and a hydrophobic filter medium mounted in said housing between said inlet and said outlet, the connection between said housing and said filter medium being sufficiently sealed to prevent substantial leakage of gas passing through said housing and cause substantially all of said gas to pass through said filter medium, said filter medium including a plurality of layers of hydrophobic filtering material and a plurality of layers of hydrophobic supporting pads, said layers of filtering material being sufficient in number to retain in excess of 99.0% of the bacteria in a humidified oxygen stream passing through the filter in a first group of said layers, and retard grow through of said retained bacteria in a second group of said layers of said filtering material, whereby humidified, substantially bacteria free oxygen can be supplied for life support even though the oxygen, oxygen regulating equipment or the humidifying apparatus are not sterile.

16. The system of claim 15 wherein said filter is located at the outlet of said humidifier.

17. The system of claim 15 wherein said means adapted to provide oxygen to said respiratory system is a breathing mask and said filter is an integral part of said breathing mask.

18. The system of claim 15 wherein at least four layers of said filtering material are provided.

19. The system of claim 18 wherein said support material is made from a group of material consisting essentially of nylon or rayon.

20. The system of claim 18 wherein said filtering material is made of a relatively close, randomly woven, sheet glass material.

21. The system of claim 20 wherein said support material is made from a group of material consisting essentially of nylon or rayon.

* * * * *